United States Patent
Acosta Montoya et al.

(10) Patent No.: US 10,278,949 B2
(45) Date of Patent: May 7, 2019

(54) METHOD FOR OBTAINING AN EXTRACT RICH IN ELLAGIC ACID TANNINS FROM FRUITS THAT CONTAIN THESE COMPOUNDS, AND RESULTING EXTRACT

(75) Inventors: Oscar Gerardo Acosta Montoya, San Antonio de Desamparados (CR); Ana Mercedes Perez Carvajal, Esparza de Puntarenas (CR); Manuel Dornier, Calpiers (FR); Fabrice Vaillant, San Jose, CA (US)

(73) Assignees: UNIVERSIDAD DE COSTA RICA, San Jose (CR); CENTRO INTERNACIONAL DE COOPERACION EN INVESTIGACION AGRICOLA PARA EL DESARROLLO, CIRAD, Montpellier (FR); CENTRO INTERNACIONAL DE ESTUDIOS SUPERIORES EN CIENCIAS AGRONOMICAS, SUPAGRO, Montpellier (FR)

( * ) Notice: Subject to any disclaimer, the term of this patent is extended or adjusted under 35 U.S.C. 154(b) by 233 days.

(21) Appl. No.: 14/117,282

(22) PCT Filed: May 11, 2012

(86) PCT No.: PCT/CR2012/000001
§ 371 (c)(1),
(2), (4) Date: Mar. 8, 2014

(87) PCT Pub. No.: WO2012/152232
PCT Pub. Date: Nov. 15, 2012

(65) Prior Publication Data
US 2014/0343135 A1 Nov. 20, 2014

(30) Foreign Application Priority Data
May 12, 2011 (CR) .................................. 2011-0251

(51) Int. Cl.
*A61K 31/352* (2006.01)
*C07H 1/08* (2006.01)
(Continued)

(52) U.S. Cl.
CPC .......... *A61K 31/352* (2013.01); *A23L 33/105* (2016.08); *A61C 19/004* (2013.01);
(Continued)

(58) Field of Classification Search
None
See application file for complete search history.

(56) References Cited

U.S. PATENT DOCUMENTS 7,638,640 B2 12/2009 Seeram et al.
2006/0211635 A1* 9/2006 Seeram ................ A61K 31/352
514/27
(Continued)

FOREIGN PATENT DOCUMENTS

CN 101524173 A * 9/2009
CN 102028774 A * 4/2011
(Continued)

OTHER PUBLICATIONS

Aehle, W: Enzymes in Industry; Verlag GmbH & Co. Weinheim, 2007, p. 120.*
(Continued)

*Primary Examiner* — Amy L Clark
(74) *Attorney, Agent, or Firm* — Brooks Kushman P.C.

(57) ABSTRACT

A biotechnology process that employs membrane technology for obtaining an extract rich in tannins of ellagic acid from blackberries (*Rubus* spp.) and from other fruits that contain these compounds, as well as to the extract obtained using this method. The method is essentially based on baromembrane technologies that allow mechanical separation and effective fractionation between the polyphenol
(Continued)

compounds, by interactions between the physico-chemical properties thereof, the material of the membrane and the molar mass of same, thereby allowing enrichment of a fraction of the natural extract with ellagic acid tannins and modification of the content thereof in terms of anthocyanins and other compounds such as sugars and acids.

20 Claims, 8 Drawing Sheets

(51) Int. Cl.
| | |
|---|---|
| C07D 493/04 | (2006.01) |
| A61K 36/87 | (2006.01) |
| A61K 36/185 | (2006.01) |
| A61K 36/605 | (2006.01) |
| A61K 36/73 | (2006.01) |
| A61K 8/49 | (2006.01) |
| A61Q 90/00 | (2009.01) |
| A23L 33/105 | (2016.01) |
| A61C 13/15 | (2006.01) |
| A61C 19/08 | (2006.01) |
| A61K 8/97 | (2017.01) |

(52) U.S. Cl.
CPC ............ *A61C 19/08* (2013.01); *A61K 8/498* (2013.01); *A61K 8/97* (2013.01); *A61K 36/185* (2013.01); *A61K 36/605* (2013.01); *A61K 36/73* (2013.01); *A61K 36/87* (2013.01); *A61Q 90/00* (2013.01); *C07D 493/04* (2013.01); *C07H 1/08* (2013.01); *A61K 2236/00* (2013.01); *A61K 2800/10* (2013.01)

(56) References Cited

U.S. PATENT DOCUMENTS

| | | | |
|---|---|---|---|
| 2006/0251753 A1 | 11/2006 | Alkayali | |
| 2006/0269629 A1 | 11/2006 | Bates et al. | |

FOREIGN PATENT DOCUMENTS

| | | | | |
|---|---|---|---|---|
| EP | 1967079 | | 9/2008 | |
| EP | 1967079 A2 | * | 9/2008 | ............ A61K 8/498 |
| WO | 2005097106 | | 10/2005 | |
| WO | WO 2005/123603 A1 | * | 12/2005 | |
| WO | WO 2006127832 A2 | * | 11/2006 | ........... A61K 36/185 |

OTHER PUBLICATIONS

Filho et al. Tangential Microfiltratoin of Orange Juice in Bench Pilot; Cienc. Tecnol. Ailment., Campinas, 23(3): 330-336 (2003).*
Hager et al. Ellagitannin Composition of Blackberry as Determined by HPLC-ESI-MS and MALDI-TOF-MS; J. Agric. Food Chem. 2008, 56, 661-669.*
Houp, R. Ultrafiltration and Diafiltration; Biotech Processes, Journal of Validation Technology; Autumn 2009, pp. 40-45.*
Mertz: Analysis of Phenolic Comopunds in Two Blackberry Species (*Rubus glaucus* and *Rubus adenotrichus*) by High-Performance Liquid Chromatography With Diode Array Detection and Electrospray Ion Trap Mass Spectrometry; j. Agric. Food Chem. 2007, 55, pp. 8616-8624.*
Muilenberg, T. Microfiltration: How Does It Compare? Water and Waste Digest Online, URL: < http://www.wwdmag.com/desalination/microfiltration-how-does-it-compare > Dec. 28, 2000 08:16, 3 pages.*
Wei et al. Concentration of Rutin Model Solutions From Their Mixtures With Glucose Using Ultrafiltration; Int. J. Mol. Sci. 2010, 11, pp. 672-690.*
(X1) Beveredge, T. Crit Rev Food Sci Nutr. Aug. 1997;37(5):449-469.*
(U2) Toledo, R. "Chapter 13: Physical Separation Process". from Fundamentals of Food Process Engineering (2007) pp. 475-511.*
(V2) Short et al. "Crossflow Microfiltration in the Food Industry" from Effective Industrial Membrane Processes: Benefits and Opportunities. Turner, MK, Ed., pp. 181-189.*
International Search Report for PCT/CR2012/000001, English translation attached to original, Both completed by the European Patent Office on Aug. 29, 2012, All together 5 Pages.
Dell'Agli et al. Malaria Journal 2010, vol. 9, 9 Pages, "Ellagitannins of the fruit rind of pomegranate (*Punica granatum*) antagonize in vitro the host inflammatory response mechanisms involved in the onset of malaria."
Adams et al. Cancer Prevention Research 2010, vol. 3, p. 108-113, "Pomegranate Ellagitanin-Derived Compounds Exhibit Antiproliferative and Antiaromatase Activity in Breast Cancer Cells in vitro."
Viuda-Martos et al. Comprehensive Reviews in Food Science and Food Safety 2010, vol. 9, p. 635-654, "Pomegranate and its Many Functional Components as Related to Human Health: A Review."
Barrajon-Catalan et al. Food and Chemical Toxicology 2010, vol. 48, p. 2273-2282, "Cistaceae aqueous extracts containing ellagitannins show antioxidant and antimicrobial capacity, and cytotoxic activity against human cancer cells."
Acosta-Montoya et al. Food Chemisty 2010, vol. 19, p. 1497-1501, "Phenolic content and antioxidant capacity of tropical highland blackberry (*Rubus adenotrichus* Schltdl.) during three edible maturity stages."
Freshney, Culture of Animal Cells 2005, 566 Pages, "A Manual of Basic Technique."
Hager et al. Journal of Agricultural and Food Chemistry 2008, vol. 56, p. 661-669, "Ellagitannin Composition of Blackberry as Determined by HPLC-ESI-MS and MALDI-TOF-MS."
Kasimsetty et al. Journal of Agricultural and Food Chemistry 2010, vol. 58, p. 2180-2187, "Colon Cancer Chemopreventive Activities of Pomegranate Ellagitannins and Urolithins."
Sharma et al. Journal of Agricultural and Food Chemistry 2010, vol. 58, p. 3965-3969, "Effects of Fruit Ellagitannin Extracts, Ellagic Acid, and Their Colonic Metabolite, Urolithin A, on Wnt Signaling."
Mertz et al. Journal of Agricultural and Food Chemistry 2007, vol. 55, p. 8616-8624, "Analysis of Phenolic Compounds in Two Blackberry Species (*Rubes glaucus* and *Rubus adenotrichus*) by High-Performance Liquid Chromatography with Diode Array Detection and Electrospray Ion Trap Mass Spectrometry."
Pinto et al. Journal of Medicinal Food 2010, vol. 13, No. 5, p. 1027-1035, "Evaluation of Antiproliferative, Anti-Type 2 Diabetes, and Antihypertension Potentials of Ellagitannins from Strawberries (Fragaria x ananassa Duch.) Using In Vitro Models."

\* cited by examiner

METHOD FOR OBTAINING AN EXTRACT RICH IN ELLAGIC ACID TANNINS FROM FRUITS THAT CONTAIN THESE COMPOUNDS, AND RESULTING EXTRACT

CROSS-REFERENCE TO RELATED APPLICATION

This application is the U.S. national phase of PCT Application No. PCT/CR2012/000001 filed on May 11, 2012, which claims priority to Costa Rica Patent Application No. 2011-0251 filed on May 12, 2011, the disclosures of which are incorporated in their entirety by reference herein.

TECHNICAL FIELD

This invention is related to the field of biotechnology and the processes that use membrane technology, and specifically refers to a method for obtaining an extract rich in ellagitannins from the blackberry fruit and from other fruits containing these compounds, and the extract obtained using said method.

BACKGROUND OF INVENTION

Ellagitannins are compounds that belong to the class of polyphenols called hydrolyzable tannins, and are complex derivatives of ellagic acid. Recently, it has been suggested that ellagitannins (in addition to the ellagic acid produced after its hydrolysis and the urolitin—which is derived from this molecule due to the action of the intestinal flora) present a series of biological activities that are beneficial to human health. Specifically, among others, these compounds: (1) have a high potential for the treatment of hyperglycemia and hypertension associated to type 2 diabetes (Pinto Mda, S. et al, Journal of Medicinal Food, 2010, 13 (5), 1027-1035), (2) could be used in the treatment of malaria (Dell'Agli, M. et al, Malaria Journal, 2010, 9, 208), (3) have the potential to be used in the prevention of breast cancer (Adams, L. S. et al, Cancer Prevention Research, 2010, 3, 108) and (4) could reduce the risk of developing cancer of the colon (Kasimsetty, S. G. et al, Journal of Agricultural and Food Chemistry, 2010, 58 (4), 2180-2187 and Sharma, M. et al, Journal of Agricultural and Food Chemistry, 2010, 58 (7), 3965-3969). Other studies of plant extracts containing ellagitannins demonstrated their antioxidant and antimicrobial properties as well as their cytotoxic activity against human cancer cells (Barrajón-Catalan, E. et al, Food and Chemical Toxicology, 2010, 48 (8-9), 2273-2282).

In recent years, the pomegranate (*Punica granatum* L.) has been studied extensively because of the therapeutic applications that have been reported for this fruit since ancient times, and it has been demonstrated recently that this fruit acts as an antioxidant, anti-diabetic and hypolipidemic agent. It has also been observed that this fruit presents antibacterial, anti-inflammatory, antiviral and anti-carcinogenic activities. These benefits have been attributed to the phytochemicals contained in the fruit, which are primarily polyphenols, that, in turn, mainly include hydrolyzable tannins, of which ellagitannins are the most important (Viuda-Martos, M. et al, Comprehensive Reviews in Food Science and Food Safety, 2010, 9 (6), 635-654). The vast potential for the therapeutic use of pomegranate has resulted in that a large part of the scientific literature available on ellagitannins refers to those obtained from this fruit. However, it was recently discovered that the blackberry (the fruit produced by some of several species of the *Rubus* genus, of the Rosaceae family), specifically *Rubus adentrichos* Schltdl., could very well have a high ellagitannin content than that of the pomegranate (Acosta-Montoya, O. et al, Food Chemistry, 2010, 119(4), 1497-1501). The high concentrations of these molecules in blackberries at different stages of ripening, make them a raw material of potential interest in the production of extracts that are rich ellagitannins.

Figure 1:
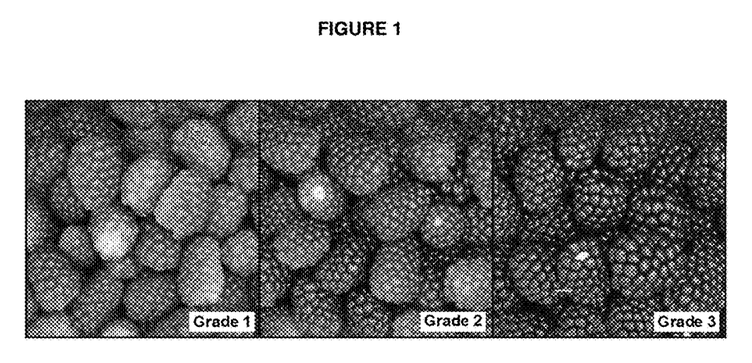
FIG. 1 shows the blackberries (*Rubus adentrichos* Schltdl.) used in the study conducted before the invention, in order to establish the chemical composition of the fruits for three different stages of ripening.
Figure 2:
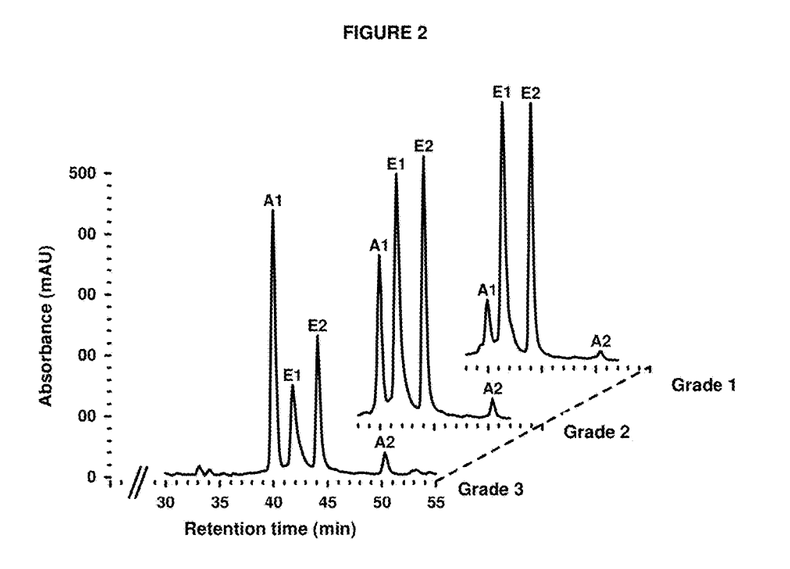
FIG. 2 shows the segments of the chromatograms obtained through high performance liquid chromatography coupled to a diode array detector (HPLC-DAD) at 280 nm of the aqueous-ketone blackberry extract for the three stages of ripening, from the study referred to above.

The blackberries used in the study mentioned above can be used at the three stages of ripening presented (FIG. 1). The chromatogram segments (high performance liquid chromatography coupled to a diode array detector or HPLC-DAD) at 280 nm of the aqueous—ketone blackberry extract for this study are shown on FIG. 2. As it can be observed, compounds A1, A2 and E1, E2 show spectral features in the ultraviolet visible (UV-visible) of anthocyanins (A1, A2) and ellagitannins (E1, E2). These molecules were identified using liquid chromatography coupled with mass spectrometry (HPLC-MS) and UV visible data from a previous study (Mertz, C. et al, Journal of Agricultural and Food Chemistry, 2007, 55 (21), 8616-8624). Peaks A1 and A2 were tentatively identified as cyanidin glucoside and cyanidin malonyl-glucoside, while peaks E1 and E2 were identified as lambertianin C and sanguin H6. The mentioned study further shown that blackberries of the *Rubus glaucus* species are also an important source of ellagitannins. Other studies have shown the variety of these compounds that are found in the Apache blackberry (Hager, T. J. et al, Journal of Agricultural and Food Chemistry, 2008, 56 (3), 661-669).

Methods for obtaining extracts from sources that are rich in ellagitannins (purified to a greater or lesser extent) have been extensively investigated, particularly with regard to the use of pomegranates as a source for these compounds. Several scientific publications, primarily patent applications, have been published on this subject.

Document US 2006/0269629 discloses a method for producing an extract containing phytochemicals from pomegranate, by creating a mixture of solids from fruits (pericarp, seeds, etc.) with water, adding enzymatic preparations to degrade the solids (at least partially), increasing the temperature of the mixture and, ultimately, removing the residual insoluble solids. Document US 2006/0211635, in turn, presents a method for the purification of ellagitannins found in pomegranate, by carrying out extraction and purification stages with the implementation of extractions using solvents (such as methanol) and chromatography with solid polymeric adsorbents. In the same manner, document WO 2005/097106 describes a similar technique, based on extraction and purification using a solid polymeric adsorbent.

Document US 2006/0251753 presents a method for the production of an extract containing ellagitannins derived from pomegranate plant materials. To obtain this product, consecutive extractions are carried out with solvents such as ethanol and acetic ether, with the final concentration carried out under vacuum.

Document EP 1967079 discloses a method for the preparation of pomegranate extracts using whole fruits, which are broken up and dispersed in water. After this, the pH is adjusted and clarification through filtration or centrifugation is carried out, adsorption occurs in a non-ionic resin and elution is produced with an aqueous solution. Lastly, it is concentrated by reverse osmosis or nanofiltration and dehydrated by spray drying, vacuum evaporation or lyophilization.

The examples described above have several drawbacks. Some of these processes require the use of solvents for the extraction of the molecules of interest or to carry out desorption of said molecules from the resins (when using solid polymeric adsorbents). Therefore, the final product obtained could contain solvent residues, resulting in an extract that cannot be qualified as "natural". Other processes described may include the excessive addition of water for the extraction of the compounds of interest from the solids of fruits, which significantly affects the efficiency of the process due to an essential concentration stage would be required, increasing the energy costs. Other techniques require that concentration be carried out under vacuum, which could cause thermal damage to the molecules of interest, thus affecting the functionality of the finished product.

To date, no process has been disclosed that allows for the separation, purification and concentration of ellagitannin, without the use of solvents or high temperatures. In particular, no process has been described that allows separating the polyphenolic compounds of interest (ellagitannins) by using the interactions between their physic-chemical properties and the membrane material, in addition to consider its molar mass.

SUMMARY OF THE INVENTION

One object of the this invention is to obtain a natural extract from fruits containing ellagitannins, specifically from the blackberry, and particularly from the fully mature *Rubus adentrichos* Schltdl. blackberry, an extract that is rich with ellagitannins and may optionally include different amounts of anthocyanins, sugars and acids. The extract of this invention does not contain chemical residues because the method used for the extraction does not involve chemical solvents. In a particular embodiment of the invention, the raw material used to obtain the extract can be the solid waste obtained after the extraction of the juice from blackberry.

To obtain the extract of the invention, membrane technologies are applied which allow a mechanical separation or effective fractionation between the polyphenolic compounds in the extract, according to their molar mass and depending on their affinity for the membranes, making it possible to enrich one of the extract fractions with ellagitannins and to modulate the anthocyanin content (apart from sugars and acids) in it, by choosing the membrane material for this and regulating its filtration capacity and the transmembrane pressure applied in the process.

In contrast with other techniques, the method of the invention does not use chemical solvents, which entails a significant reduction in process costs and greater preservation of the quality of the extract obtained.

In summary, it can be said that the invention consists in the development of a process comprising an extraction stage or step by using enzymatic preparations and pressing operations, a clarification stage by microfiltration to remove the insoluble solids in suspension, a fractionation stage by ultrafiltration or nanofiltration, that enables the separation of ellagitannins from the other soluble compounds, a purification stage by diafiltration and finally a concentration stage.

By applying the process described, the resulting product has a high concentration of ellagitannins (for the *Rubus adentrichos* Schltdl. blackberry, these correspond to lambertianin C and sanguine H6), a changeable concentration of anthocyanins and other water-soluble molecules (such as sugars) and low concentrations of organic acids.

The present invention establishes that while ellagitannins present molecular weights between 1 800 and 2 900 Da, and anthocyanins between 450 and 550 Da, it is quite surprising that during ultrafiltration with membranes with a filtration capacity of up to 50 000 Da, 100% of ellagitannin retention is obtained, while a partial retention of anthocyanins is observed, which means that, from a technical standpoint, the separation of ellagitannins is much easier and less expensive than might be envisaged, if the process of this invention is applied for that purpose.

The proposed invention can also be applied to all fruits containing ellagitannins, such as (but not limited to) the pomegranate, raspberry, strawberry, grape, blackberry and several other species of *Rubus* genus, but preferably the blackberry.

Regarding the specific use of the extract that is obtained with this invention, it is anticipated that it can be used in the food industry as an additive (liquid or powder, if dehydrated with conventional technologies such as lyophilization or spray drying) to increase ellagitannin content in liquid foods such as juices or drinks, or in solid foods such as cereal and fruit bars, breakfast cereals, and others.

Since the extract produced by the method of the invention could undergo a change in coloration due to the decrease of the anthocyanin content, this would also allow for a broader application of the product, in the pharmaceutical industry for the production of medications with specific properties, in the food industry in the making of nutritional supplements, and also in the cosmetic industry.

Therefore, one object of the present invention is to provide a method for obtaining an extract that is rich in ellagitannins from fruits containing these compounds (particularly the fully mature *Rubus adentrichos* Schltdl. and *Rubus glaucus* blackberries). Said method comprising the stages of:

extraction of the liquid fraction from fruit or fruit wastes by pressing and using enzymes;

clarification of the liquid fraction obtained in stage (i) through tangential microfiltration;

permeate fractionation after the tangential microfiltration stage;

(ii) through ultrafiltration and nanofiltration;

purification by diafiltration of the fraction retained by the membrane in the previous filtering process (iii); and final concentration of an ellagitannin rich extract using thermal and athermal technologies such as reverse osmosis, osmotic evaporation or combined processes.

Figure 3:
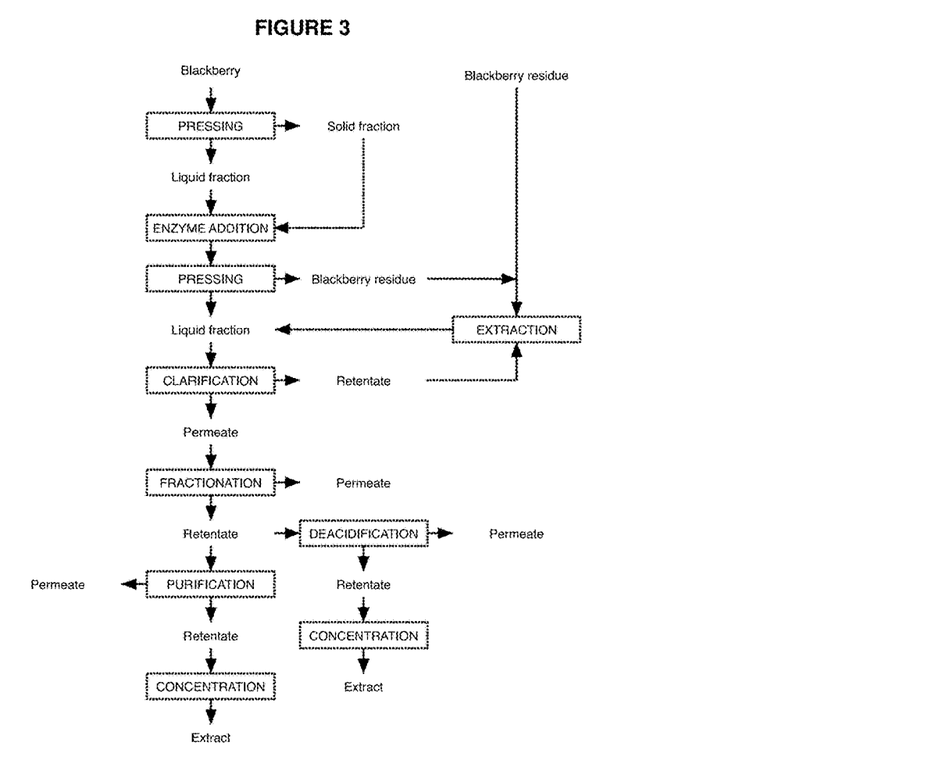
FIG. 3 presents a flow chart for the method of the present invention for obtaining of an extract rich in ellagitannins from the blackberry fruit.

FIG. 3 shows a flow chart for the method of the present invention, detailing the stages mentioned above.

In the method provided by the invention, a mechanical pressing process that is carried out in conjunction with an enzyme treatment using cellulolytic and pectinolytic enzymes, or mixtures and combinations of said enzymes, it is achieved the extraction of the molecules of interest.

When fruits are used as the raw material, pressing is carried out under certain operating conditions that are important to the result obtained, such as, for example: pressing may be continuous or discontinuous, with an applied pressure between 2 000 and 10 000 kPa, for periods of time between 5 and 40 minutes, against a mesh with an aperture size between 0.2 and 1 mm. The juice obtained is then mixed again with the solid residues and an enzymatic preparation is added, which has at least one pectinase activity corresponding to a polygalacturonase activity (EC 3.2.1.15) higher than 100 $UE \cdot mL^{-1}$ (and/or a pectin lyase activity (EC 4.2.2.10) higher than 100 $UE \cdot mL^{-1}$) and at least one cellulase activity corresponding to an endocellulase activity (EC 3.2.1.4) higher than 20 $UE \cdot mL^{-1}$ and/or an exocellulase activity (EC 3.2.1.91) higher than 1 $UE \cdot mL^{-1}$. A concentration of the enzymatic preparation between 10 and 500 mg·kg$^{-1}$ is used, with temperatures between 20 and 50° C., and action times between 30 and 90 minutes.

Enzymatic activities are expressed in EU (Enzymatic Units), that is to say, in micromoles of reducing groups released from a standard substrate. Said substrates include polygalacturonic acid for the polygalacturonase activity (EC 3.2.1.15); highly esterified citric pectin (80%) for the pectinlyase activity (EC 3.2.1.4) and crystalline cellulose for the exocellulase activity (EC 3.2.1.91). The standard experimental conditions for the determination of these enzymatic activities are as follows, respectively: pH 4 at 30° C.; pH 6 at 40° C.; pH 4.6 at 38° C. and pH 4.8 at 50° C.

Pressing is applied again, under certain operating conditions: which may be continuous or discontinuous, with an applied pressure between 2 000 and 10 000 kPa, for periods of time between 5 and 40 minutes and against a mesh with an aperture size between 0.2 and 1 mm.

The previous stage allows for the removal of large part of the insoluble solids in suspension, such as residues from the cell walls and seeds. The liquid fraction obtained after this stage has a high extraction yield for polyphenolic compounds, allowing to extract between 60 and 90% of the initial content of anthocyanins and ellagitannins.

When using fruit wastes as the raw material, the compounds of interest are extracted under certain operating conditions that are important to the result obtained. Said conditions are, for example: the addition of water, that has been previously acidified to a pH between 3.0 and 5.0, in varying proportions in relation to the mass of residue between 1 and 10, allowing the mixture to stand for a period of time between 20 and 120 minutes, at a temperature that is kept between 20 and 50° C., with varied or constant stirring. An enzymatic preparation that has at least one pectinase activity corresponding to a polygalacturonase activity (EC 3.2.1.15) higher than 100 EU·ml$^{-1}$ (and/or a pectinlyase activity (EC 4.2.2.10) higher than 100 EU·ml$^{-1}$) and at least one cellulase activity corresponding to an endocellulase activity (EC 3.2.1.4) higher than 20 UE·mL$^{-1}$ and/or an exocellulase activity (EC 3.2.1.91) higher than 1 EU·mL$^{-1}$ is then added. An enzymatic preparation concentration between 10 and 500 mg·kg$^{-1}$ is used, with temperatures between 20 and 50° C., and action times between 30 and 90 minutes.

After the extraction period, the solids are removed by filtration through a mesh with an aperture size between 1 and 5 mm. This extraction process can be repeated consecutively 1 to 4 times, retaining and mixing the aqueous fractions.

Finally, pressing is applied to the solid residue, which may be continuous or discontinuous, with pressures of between 2 000 and 10 000 kPa, for 5 to 40 minutes, using a mesh aperture size between 0.2 and 1 mm. The resulting liquid is mixed with the aqueous fractions obtained in the previous stage.

This stage of pressing and enzymatic extraction allows for the removal of a large part of the insoluble solids in suspension, such as residues from the cell walls and seeds. The liquid fraction obtained after this stage has a high extraction yield of polyphenolic compounds, allowing to extract between 30 and 90% of the initial content of anthocyanins and ellagitannins.

The liquid fraction obtained in the previous stages is then clarified using microfiltration technology, with a membrane that can be either organic or inorganic, preferably with a pore size between 0.05 and 1.0 μm. The operation is carried out under certain conditions such as: a tangential velocity between 4 and 7 m·s$^{-1}$, a transmembrane pressure between 120 and 350 kPa, and a temperature between 25 and 50° C. This filtration is continued until a volume reduction factor (VRF) between 5 and 30 is obtained.

As a result of the tangential microfiltration, all of the insoluble solids suspended in the extract are removed, the permeate is microbiologically stable (if pore sizes below 0.2 microns are used) and a high concentration of polyphenolic compounds is obtained in this fraction (compounds of interested are not retained during this operation).

The retentate resulting after the microfiltration operation can be considered as fruit residue, and compounds of interest can be extracted by following the stages above described.

After the stage that completely removes the insoluble solids in suspension by microfiltration, a permeate containing only soluble solids is obtained, which then is submitted again to a membrane separation (fractionation), specifically ultrafiltration or nanofiltration, with an organic or inorganic membrane, that is tubular or flat, with a filtration capacity between 0.1 and 50 kDa, and an applied transmembrane pressure between 250 and 4 000 kPa. This operation is carried out under certain conditions: a tangential velocity between 0.2 and 4 m·s$^{-1}$, and a temperature between 25 and 50° C. The operation is continued until a volume reduction factor (VRF) between 5 and 30 is obtained.

In this new fractionation, it is observed that the soluble molecules, such as anthocyanins, sugars and acids, are not fully retained in the membrane and a portion can pass on to the permeate, depending on the retention degree. The ellagitannins are completely retained by the membrane, which makes it possible to carry out the separation and concentration of these molecules.

From these ultrafiltration or nanofiltration operations, two fractions are obtained:
(a) a permeate that is a liquid fraction with a high concentration of primarily soluble molecules such as sugars and acids. This fraction may contain anthocyanins in varying amounts, depending on the filtration capacity of the membrane and the transmembrane pressure applied, and
(b) a retentate that is also a liquid fraction with a high concentration of ellagitannins, a varied concentration of anthocyanins and a low concentration of other soluble molecules, such as sugars and acids. The concentration of ellagitannins in the retentate is directly proportional to the VRF obtained during ultrafiltration and also depends on the concentration of molecules in the raw material used for this stage.

The retentate obtained in the previous stage is purified through diafiltration, using an organic or inorganic membrane, that is tubular or flat, with a filtration capacity between 0.1 and 50 kDa, and an applied transmembrane pressure between 250 and 4 000 kPa. This operation is carried out under certain conditions: a tangential velocity between 0.2 and 4 m·s$^{-1}$, and a temperature between 25 and 50° C. Diafiltration is carried out at a constant volume, adding purified water at the same flow rate as the permeate. This filtration is continued until a purity of 90%, with regards to the other soluble solids present in the retentate, is obtained for the ellagitannins.

This diafiltration stage is designed to facilitate the separation of ellagitannis from other soluble molecules. Thus, it is observed the same effect described for the fractionation stage: soluble molecules such as anthocyanins, sugars and acids, are not fully retained in the membrane and pass into the permeate. Since the acids pass through ultrafiltration and nanofiltration membranes when washed through with water, a deacidification of the extract also occurs, which eliminates up to 80% of retained acids. The ellagitannins are completely retained by the membrane, which makes it possible to carry out the purification of these molecules.

From this diafiltration operation, using the same membranes and conditions used in the fractionation stage, two fractions are again obtained:
(a) a permeate that is a liquid fraction with a high concentration of primarily soluble molecules such as sugars and acids, and
(b) a retentate that is also a liquid fraction with a high concentration of ellagitannins, and a low concentration of primarily soluble molecules, such as anthocyanins, sugars and acids. This stage does not result in the concentration of ellagitannins because the volume of the retentate remains constant, but there is a purification of these molecules due to the output of anthocyanins, sugars and acids through the permeate.

The retentates obtained during the fractionation (through ultrafiltration and nanofiltration) and purification (through diafiltration, with ultrafiltration and nanofiltration membranes) stages can be further concentrated under thermal or athermal conditions, and preferably under the latter so as to minimize the degradation of the compounds of interest. In particular, conventional technologies may be used or athermal membrane technologies, such as osmotic evaporation and reverse osmosis may also be used. Said extract concentrate may then be dehydrated through conventional technologies, such as lyophilization or spray drying, thereby resulting in a powdered extract.

The method of the invention is particularly useful for obtaining an extract with a high ellagitannin content, when fruits such as the tropical mountain blackberry *Rubus adentrichos* Schltdl. or *Rubus glaucus* are used as the raw materials.

The ellagitannin rich extract that is the object of the present invention, is characterized by having a content of these compounds that makes up between 50 and 90% of the mass on dry basis, with an anthocyanin content that may vary between 0 and 50% of the mass on dry basis, depending on the filtration capacity of the membranes and the transmembrane pressure applied during filtration stages that are carried out as part of the process of the invention.

Other additional objects of the invention are a nutritional composition comprising the extract obtained through the process of the invention that also includes a nutritional acceptable excipient; a pharmaceutical composition comprising the extract and a pharmaceutically acceptable excipient and a cosmetic composition comprising the extract and a cosmetically acceptable excipient.

The present invention will be described in further detail in the following examples of its embodiments, which are presented as an illustration of the invention and should, in no way, limit its scope.

The present invention will be described in further detail in the following examples of its embodiment, which are presented as an illustration of the invention and should in no way limit its scope.

DETAILED DESCRIPTION OF THE INVENTION

Example 1: Mechanical and Enzymatic Extraction of a Liquid Fraction with High Content of Ellagitannins from Blackberry Fruits Starting raw materials contain high concentrations of ellagitannins, particularly are the fruits of the tropical mountain blackberry *Rubus adentrichos* Schltdl or *Rubus glaucus*, or the residues that results after the juice extraction from said fruit. This raw material primarily contains polyphenolic compounds such as the anthocyanins and tannins mentioned. Table 1 shows the average relevant typical composition of 9 samples of mature *R. adenotrichus* blackberries.

Table 1. Chemical Properties of the *R. adentrichos* Blackberry *

TABLE 1

Chemical properties of the *R. adentrichos* blackberry *

| Assessed parameter | | Wet basis | Dry basis |
|---|---|---|---|
| Moisture (g · 100 g of sample$^{-1}$) | | 83.8 ± 0.5 | NA |
| Anthocyanins (mg cyanadin-3-glucoside · g of sample$^{-1}$) | | 1.22 ± 0.05 | 7.6 ± 0.2 |
| Ellagitannins (mg ellagic acid · g of sample$^{-1}$) | | 3.0 ± 0.1 | 19 ± 2 |
| Antioxidant capacity (ORAC) (μmol TE · g of sample$^{-1}$) | | 74 ± 3 | 466 ± 18 |
| Soluble solids (° Brix) ** | | 9.1 ± 0.1 | NA |
| pH | | 2.61 ± 0.01 | NA |
| Acidity (g malic acid · 100 g of sample$^{-1}$) | | 2.22 ± 0.06 | 13.9 ± 0.5 |
| Sugars | Glucose | 1.48 ± 0.06 | 9.2 ± 0.4 |
| (g · 100 g of sample$^{-1}$) | Fructose | 1.5 ± 0.1 | 9.6 ± 0.8 |
| | Sucrose | ND *** | ND *** |

Average ± confidence interval (n = 9), confidence interval of 95%,
** Data corrected for acidity,
*** Less than 0.2 g · 100 g of sample$^{-1}$,
NA = not applicable,
ND = not detected,
TE = Trolox Equivalent The mentioned starting raw material (in this case the verity of blackberry *Rubus adentrichos*, completely ripen) is submitted to a mechanical-enzymatic extraction. The blackberries, which are usually supplied in a frozen state, are thawed for 36 hours at 2° C. Then, the liquid fraction is extracted through discontinuous pressing with a press, such as a Hydraulic Shop Press OTC 25 Ton, by applying 3 000 kPa of pressure on the fruit (which is located in a mesh with an aperture size of 0.7 mm) for 10 minutes.

The liquid and solid fractions obtained are then mixed in an appropriate container, heat is applied until the mixture reaches 35° C., and an enzymatic preparation, selected from those shown in Table 2, is added.

TABLE 2

Activities of the enzymatic preparations used in the extraction of blackberry juice.

| | Activity (UE · mL$^{-1}$) | | | | |
|---|---|---|---|---|---|
| Enzymatic preparation | Pectin-lyase | Poly-galacturonase | Pectin-esterase | Endo-cellulase | Exo-cellulase |
| Klerzyme 150 ®* | 344 | 866 | 409 | 112 | 4 |
| Clarex Citrus 12 XL ®* | 317 | 549 | 350 | 112 | 36 |
| Rapidase Vegetable Juice ®* | 188 | 369 | 433 | 124 | 10 |

DSM Food Specialties

The action time for the enzymatic preparation is 75 minutes, during which the temperature should be maintained at 35° C. After this, the pressing operation is applied again, which in this case may be discontinuous, for example, using the press Hydraulic Shop Press OTC 25 Ton, with a mesh aperture size of 0.7 mm, and an applied pressure of 3500 kPa for 15 minutes, or continuously, for example, using the Chisholm Ryder screw press, with a mesh aperture size of 0.9 mm, and an applied pressure of 2000 kPa.

Figure 4:
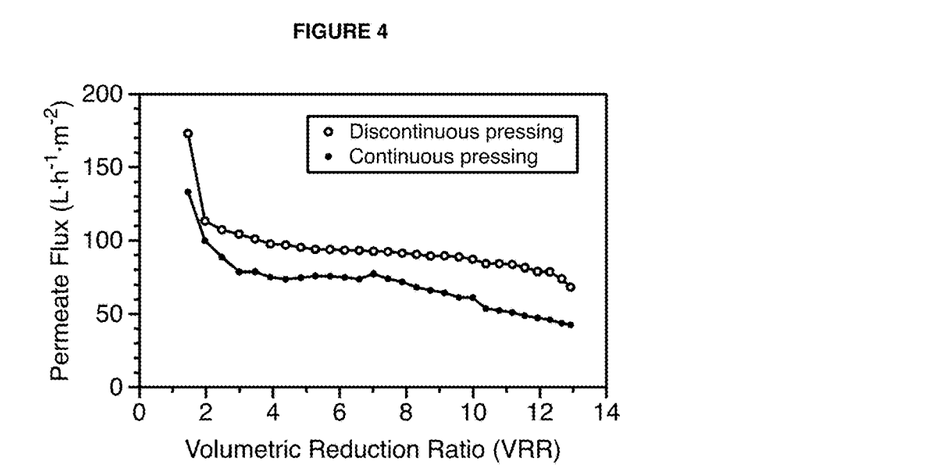
FIG. 4 shows the evolution of the permeate flow when the VRF is varied during the microfiltration operation. It presents the results obtained by applying two forms of extraction from raw materials: continuous or discontinuous pressing.

FIG. 4 shows the evolution of the permeate flow ($L \cdot h^{-1} \cdot m^{-2}$) when the VRF is varied during the microfiltration operation, according to the raw materials used in this operation, whether continuous or discontinuous pressing is applied. As it can be observed from this figure, the permeate flow values obtained when discontinue pressing is applied for extracting the juice from the raw material, are higher than the ones obtained with continue pressing. This is due to the presence of a higher concentration of suspended insoluble solids in the juice supplied when using continuous pressing, which can cause increased clogging of the membrane and therefore a decrease in the flow of the permeate.

The enzymatic concentration applied in each of previous stages should preferably be 250 mg·kg$^{-1}$ or higher. Table 3 shows the results of raw juice yields obtained and the concentrations of the compounds of interest therein, by varying the concentration of the Klerzyme 150® enzymatic preparation.

The activity of the enzymatic preparation is considerable, as seen in Table 4, where it can be seen the effect of the addition of the Klerzyme 150 ® enzyme on the juice yield obtained and the concentration of the compounds of interest therein.

TABLE 3

Changes in the varied results measured when evaluating the effect of the concentration of the enzymatic preparation Klerzyme 150 ®, applied for obtaining a liquid fraction enriched in the compounds of interest from blackberries.

| Concentration of enzymatic preparation (mg · kg$^{-1}$) | Anthocyanins (mg cyanadin -3-glucoside · g of sample$^{-1}$) | Ellagitannins (mg ellagic acid · g of sample$^{-1}$) | Juice extraction yield (g · 100 g$^{-1}$) |
|---|---|---|---|
| 1000 | 1.13 ± 0.06$^a$ | 0.93 ± 0.06$^a$ | 71.7 ± 0.8$^a$ |
| 500 | 0.98 ± 0.03$^a$ | 0.85 ± 0.08$^a$ | 70 ± 1$^{ab}$ |
| 250 | 1.13 ± 0.12$^a$ | 0.89 ± 0.10$^a$ | 68 ± 1$^{ab}$ |
| 150 | 1.12 ± 0.04$^a$ | 0.96 ± 0.07$^a$ | 66 ± 4$^b$ |
| 50 | 0.99 ± 0.12$^a$ | 0.84 ± 0.06$^a$ | 66 ± 1$^b$ |

Data reported as average ± confidence interval (n = 3), with a confidence level of 95%. Averages for the same column with different letters are significantly different (Tukey, p < 0.05).

TABLE 4

Effects of addition of the Klerzyme 150 ® enzymatic preparation, applied to obtain a liquid fraction enriched in the compounds of interest from blackberry.

| Enzymatic treatment | Anthocyanins (mg cyanadin -3-glucoside · g of sample$^{-1}$) | Ellagic acid tannins (mg ellagic acid · g of sample$^{-1}$) | Juice extraction yield (g · 100 g$^{-1}$) |
|---|---|---|---|
| Klerzyme 150 ® (250 mg · kg$^{-1}$) | 1.13 ± 0.12$^a$ | 0.89 ± 0.10$^a$ | 68 ± 1$^a$ |
| Without enzymatic preparation | 0.83 ± 0.06$^b$ | 0.63 ± 0.09$^b$ | 62 ± 3$^b$ |

Data reported as average ± confidence interval (n = 3), with a confidence level of 95%. Averages for the same column with different letters are significantly different (Tukey, p < 0.05).

Figure 5:
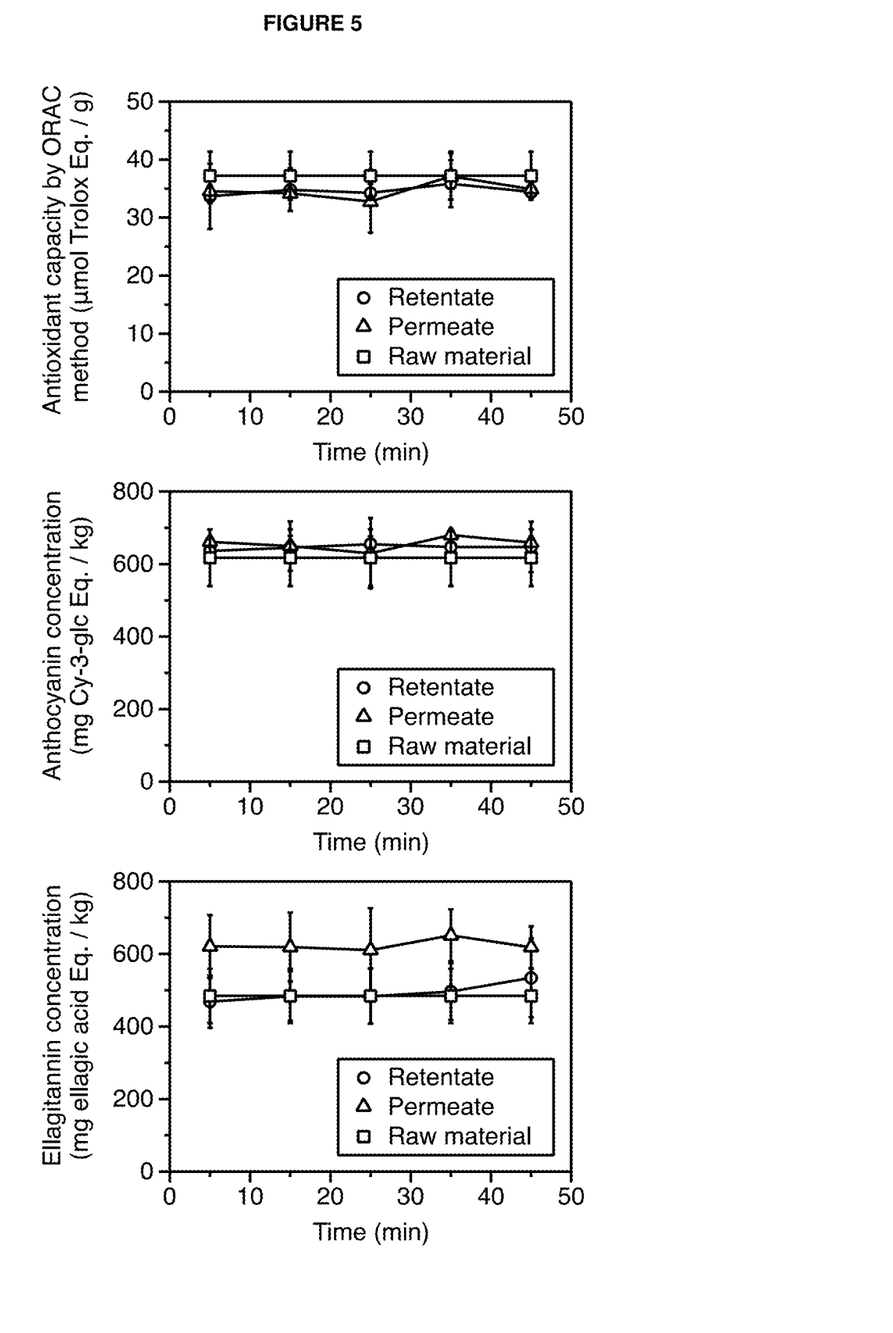
FIG. 5 shows the values for a) anthocyanin concentration, b) ellagitannin concentration and c) the antioxidant capacity of the juice fractions (permeate and retentate), according to four enzymatic preparation concentrations used (Klerzyme 150®). The values for raw materials are shown for reference. The error bars show a standard deviation for n=2.

FIG. 5 also shows that the use of different concentrations of the Klerzyme 150 ® enzymatic preparation does not significantly decrease the concentration of the compounds of interest in the permeate obtained (nor of the antioxidant capacity, measured with the ORAC method) with regards to values observed in the raw materials used, when applying the tangential microfiltration operation.

After the second pressing, liquid fractions are obtained from the blackberry fruit of the, which have characteristics that are similar to those shown in Table 5. From the information provided in this table, it can be observed that the extraction of 66 to 87% of the anthocyanins and 23 to 60% of the ellagitannins was possible. It can also be observed that the resulting juices have a low content of insoluble solids in suspension and low values of turbidity.

TABLE 5

Physic-chemical characteristics of the liquid fractions obtained from the mechanical-enzymatic extraction of blackberry fruits, using two pressing operations.

| Parameter under review | Discontinuous pressing | Continuous pressing |
|---|---|---|
| Yield (%) | 76 ± 1$^a$ | 75 ± 3$^a$ |
| Moisture (g · 100 g of sample$^{-1}$) | 92.67 ± 0.06$^a$ | 91 ± 2$^a$ |
| Soluble solids (° Brix) | 8.25 ± 0.03$^b$ | 9.00 ± 0.03$^a$ |
| pH | 2.784 ± 0.008$^a$ | 2.792 ± 0.003$^a$ |
| Acidity (g malic acid · 100 g of sample$^{-1}$) | 2.48 ± 0.06$^b$ | 2.77 ± 0.08$^a$ |
| Insoluble solids in suspension (g · 100 g of sample$^{-1}$) | 0.8 ± 0.3$^b$ | 19 ± 3$^a$ |
| Turbidity (NTU) | 218 ± 31$^b$ | 11 000 ± 2 975$^a$ |
| Anthocyanins (mg cyanidin-3-glucoside · g of sample$^{-1}$) | 0.80 ± 0.04$^b$ | 1.06 ± 0.08$^a$ |
| Ellagitannins (mg ellagic acid · g of sample$^{-1}$) | 0.7 ± 0.1$^b$ | 1.8 ± 0.3$^a$ |

Data reported as average ± confidence interval (n = 3), with a level of confidence at 95%. The averages in a same row with different letters are significantly different (Tukey, p < 0.05).

Example 2: Obtaining a Clarified Product with a High Ellagitannin Content Through Tangential Microfiltration The liquid fraction obtained during the pressing and enzymatic treatment stage, is processed through the application of tangential microfiltration, over a multichannel tubular ceramic membrane with a pore diameter of 0.2 μm, at a speed of 5 m·s$^{-1}$, the application of transmembrane pressure of 200 kPa and a temperature of 35° C. All the insoluble solids in suspension are removed with this stage and a microbiologically stable permeate is obtained, if a membrane with a pore size less than or equal to 0.2 μm is used. A clarified juice (permeate) is obtained after the microfiltration operation, that preserves the same antioxidant qualities as well as the same ellagitannin and anthocyanin concentrations of the raw material.

Figure 6:
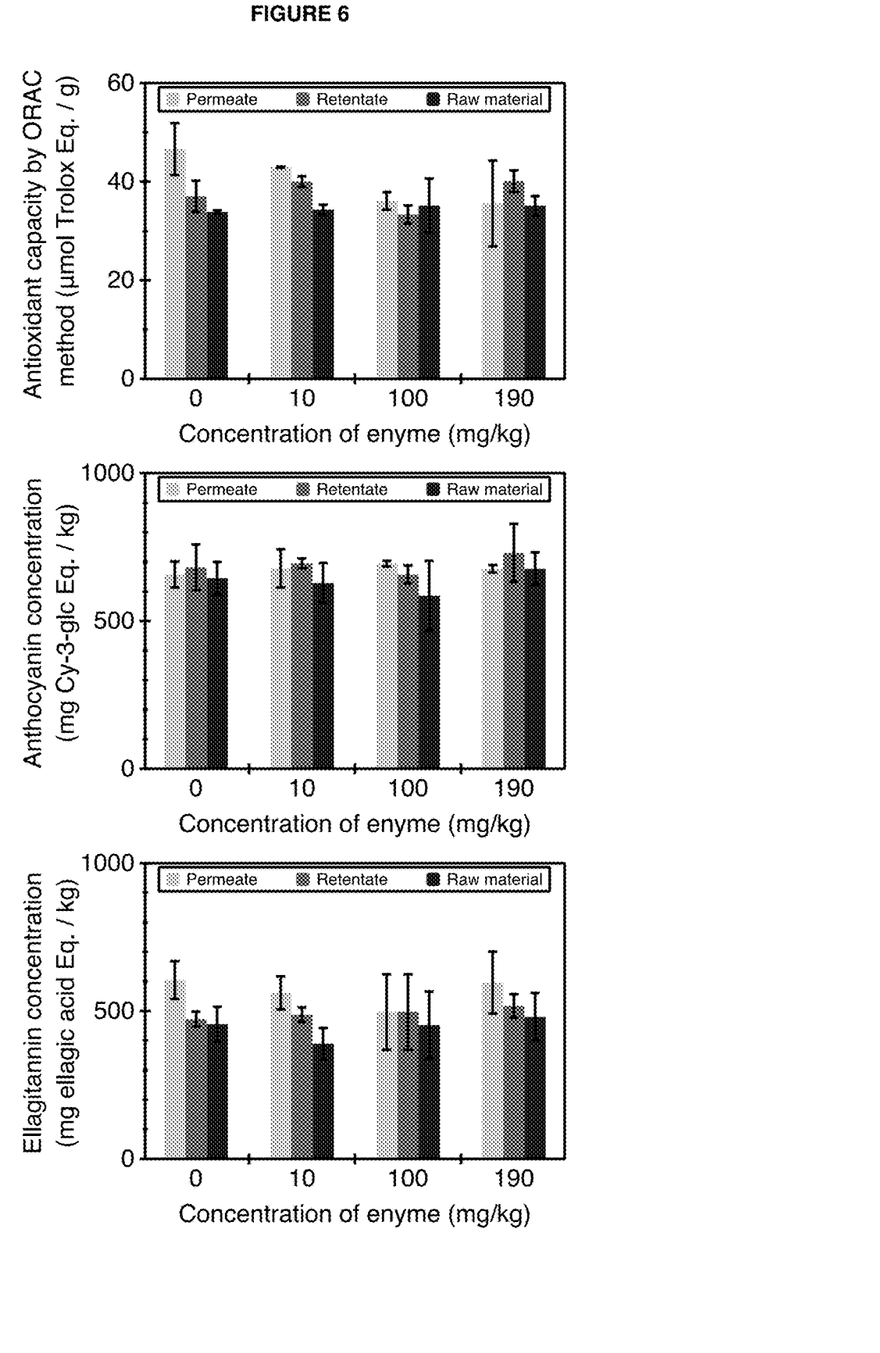
FIG. 6 shows the behavior of a) the anthocyanin concentration, b) the ellagitannin concentration and c) the antioxidant capacity of the juice fractions (permeate and retentate), throughout the course of the operation. The values for raw materials are shown for reference. The error bars show a standard deviation for n=4.
Figure 7:
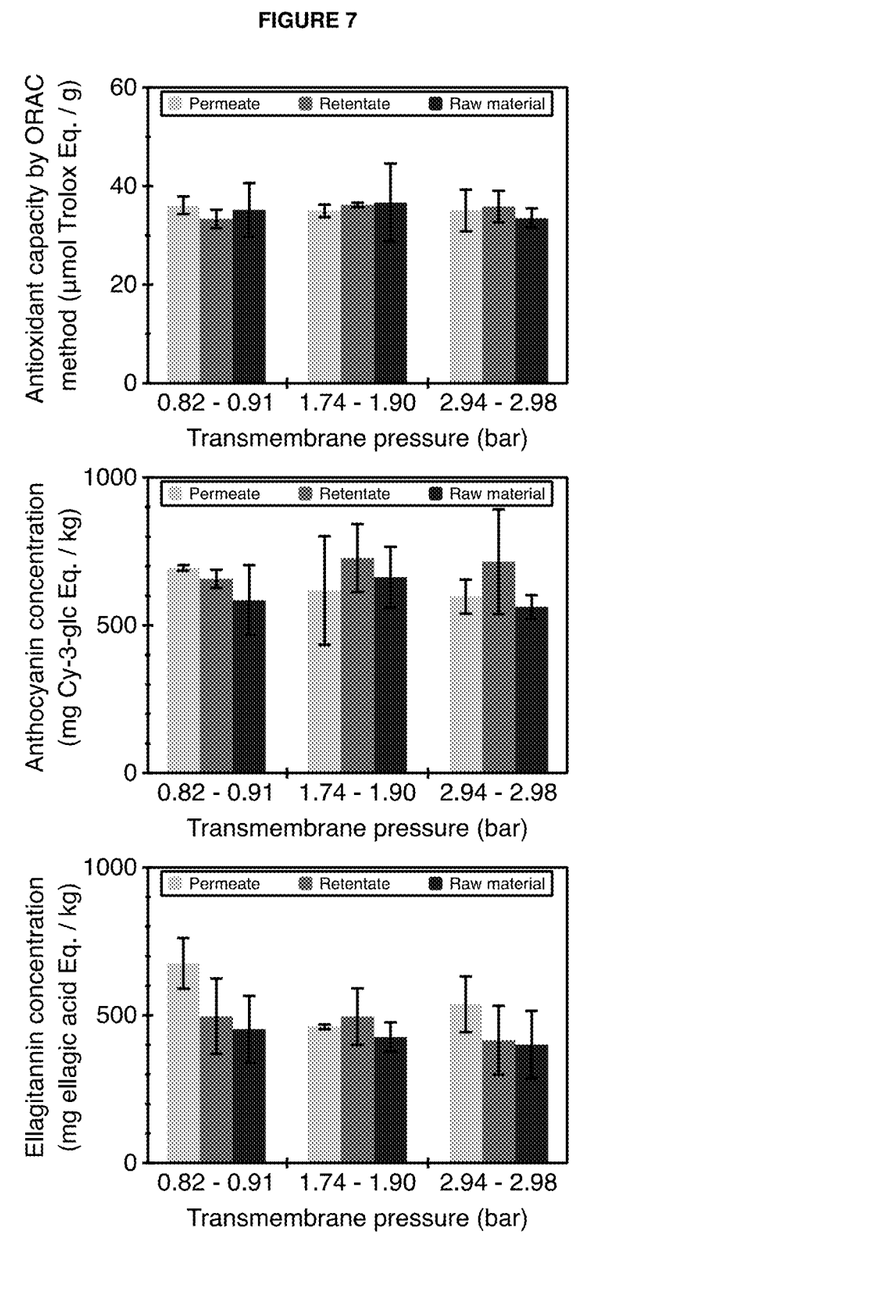
FIG. 7 shows the values for a) anthocyanin concentration, b) ellagitannin concentration and c) the antioxidant capacity of the juice fractions (permeate and retentate), according to three ranges of transmembrane pressure applied. The values for raw material are shown for reference. The error bars show a standard deviation for n=2.

FIG. 6 shows that the application of tangential microfiltration does not significantly decrease the concentration of compounds of interest in the permeate obtained (nor of the antioxidant capacity, measured with the ORAC method), in comparison to the values obtained from the raw material used, at different VRF values. FIG. 7 shows how the application of different transmembrane pressures during tangential microfiltration, does not significantly decrease the concentration of the compounds of interest in the obtained permeate (nor of the antioxidant capacity, measured with the ORAC method). On the other hand, Table 6 presents an example of the characteristics of the juice obtained before and after the tangential microfiltration.

TABLE 6

Example of characteristics for blackberry juice before and after tangential microfiltration. *

| Assessed parameter | Initial pressed juice | Microfiltrated juice |
|---|---|---|
| Moisture (g · 100 g of sample$^{-1}$) | 90.7 ± 0.2 | 90.7 ± 0.2 |
| Insoluble solids (g · 100 g of sample$^{-1}$) | 1.5 ± 0.1 | ND ** |
| Turbidity (NTU) | 452 ± 100 | 0.08 ± 0.01 |
| Soluble solids (° Brix) *** | 9.0 ± 0.3 | 9.01 ± 0.02 |
| Anthocyanin (mg cyanidin-3-glucoside · g of sample$^{-1}$) | 1.27 ± 0.03 | 1.30 ± 0.07 |
| Ellagitannins (mg ellagic acid · g of sample$^{-1}$) | 0.58 ± 0.04 | 0.64 ± 0.07 |

* Average ± confidence interval (n = 3), confidence interval of 95%,
** Less than 0.3 g · 100 g of sample$^{-1}$,
*** Data corrected for acidity,
ND = no detected Example 3: Fractionation of the Clarified Blackberry Extract, Through Ultrafiltration The permeate obtained after applying the microfiltration operation is fractionated by applying ultrafiltration membrane technology. To do this, it is selected a flat membrane, with a filtration power of 5 000 Da. The conditions of the ultrafiltration operation are: a transmembrane pressure of 3 500 kPa, a tangential speed of 2 m·s$^{-1}$ and a temperature of 35° C.

The retentates observed during the application of ultrafiltration, after 1 hour of operation (VRF of 1.13) are shown in Table 7.

TABLE 7

Retentates observed during the ultrafiltration operation of clarified blackberry juice *.

| Assessed parameter | Retention (%) |
|---|---|
| Soluble solids (° Brix) | 39.2 ± 0.2 |
| Acidity | 38.2 ± 0.8 |
| Total anthocyanins | 91.8 ± 0.7 |
| Total ellagitannins | 98.6 ± 0.2 |

* Average ± confidence interval (n = 2), level of confidence of 95%

The ultrafiltration operation is completed when a volume reduction factor (VRF) of 10 is obtained.

Example 4: Fractionation of the Clarified Blackberry Extract, Through Nanofiltration The permeate obtained after applying the microfiltration operation, is alternately fractionated by applying nanofiltration membrane technology. To do this, it is selected a flat membrane, with a filtration power of 500 Da. The conditions for the nanofiltration operation are: a transmembrane pressure of 2 000 kPa, a tangential speed of 2 m·s$^{-1}$ and a temperature of 35° C.

The retentates observed during the application of nanofiltration, after 4.5 hours of operation (VRF of 1.57) are shown in Table 8.

TABLE 8

Retentates observed during the nanofiltration operation of clarified blackberry juice *.

| Assessed parameter | Retention (%) |
|---|---|
| Soluble solids (° Brix) | 93.7 ± 0.6 |
| Acidity | 82 ± 3 |
| Total anthocyanins | 101 ± 10 |
| Total ellagitannins | 106 ± 4 |

Average ± confidence interval (n = 3), with a confidence level of 95%

The nanofiltration operation is completed when a volume reduction factor (VRF) of 10 is obtained.

Example 5: Purification of the Clarified Blackberry Extract, Through Diafiltration The retentate obtained after applying the ultrafiltration operation, is diafiltered at a constant volume, using the same membrane and the same conditions described in the ultrafiltration's operation. The retentates observed during the application of diafiltration, after 2.5 hours of operation, are shown in Table 9.

TABLE 9

Retentates observed during the diafiltration operation of the retentate obtained through ultrafiltration *.

| Assessed parameter | Retention (%) |
|---|---|
| Soluble solids (° Brix) | 47 ± 2% |
| Acidity | 41.6 ± 0.5 |
| Total anthocyanins | 96.0 ± 0.3 |
| Total ellagitannins | 98.9 ± 0.5 |

Average ± confidence interval (n = 4), level of confidence at 95%

The diafiltration operation is completed when a purity level of 80% is achieved for ellagitannins (in relation to the other polyphenols).

Example 6: Concentration of the Ellagitannin Rich Extract, Through Osmotic Evaporation The resulting product from the previous stages is concentrated through osmotic evaporation, until a concentration factor of 5 is obtained. Table 10 shows the effect of the application of osmotic evaporation on clarified blackberry juice, using a hollow fiber membrane, a saturated solution of calcium chloride as an osmotic solution, and overpressure of the product at 100 kPa. The operation was carried out at 10° C.

TABLE 10

Characteristics of clarified blackberry juices (concentrated and non concentrated)*.

| Assessed parameter | Clarified juice | Concentrated clarified juice |
|---|---|---|
| Moisture (g · 100 g of sample$^{-1}$) | 90 ± 1 | 38.43 ± 0.07 |
| Soluble solids (° Brix) | 10 ± 1 | 65.567 ± 0.007 |
| Total polyphenols (mg gallic acid · mL of sample$^{-1}$) | 2.6 ± 0.2 | 18.9 ± 0.2 |

Average ± confidence interval (n = 3), level of confidence at 95%

Example 7. Use of Micro Filtered Blackberry Juice as a Functional Food and its Protective Effect Against Oxidative Stress in Healthy Volunteers In a clinical trial conducted jointly by the Center for Science and Food Technology (CITA based on its initials in Spanish) and the Pharmaceutical Research Institute (INIFAR based on its initials in Spanish) at the University of Costa Rica, the effects of the ingestion of a drink made from microfiltered blackberry juice on specific lipid profile markers and the antioxidant capacity in 15 healthy volunteers, who were subjected to a diet rich in fat and carbohydrates for a week, were evaluated.

The group of healthy volunteers (n=15; 4 males, 11 females, average age 25±4 years, with a range of 34-20 years) underwent treatment with a beverage made from microfiltered blackberry juice and a placebo using a randomized crossover experimental design. Participants received a balanced diet low in antioxidants during the three days before the start of the study. Later, a challenge diet rich in fat and carbohydrates was administered for a week, eliminating fruits, vegetables, coffee, tea, chocolate and any known product with antioxidant qualities. During this period the participants received the blackberry beverage or placebo, as appropriate, at a volume of 250 ml per day three times a day. In order to prepare the beverage, water was added to the pure microfiltered blackberry juice at a 50/50 ratio (% m/m) and sugar ad libitum. The placebo consisted of a sugary beverage low in antioxidant activity (<0.5 micromole TE·mL$^{-1}$). The participants completed two periods of the dietary challenge with a span of three weeks between treatments. A blood sample was taken at the end of the balanced diet and at the end of the challenge diet for each period. The plasmatic concentration was measured for cholesterol, LDL, HDL and triglycerides. In addition, two enzymatic activities indicative of oxidative stress, superoxide dismutase (SOD) and catalase (CAT) were determined.

Figure 8:
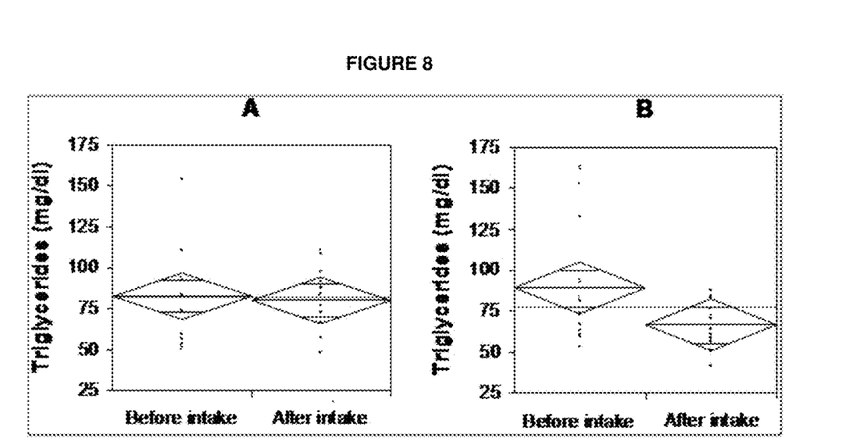
FIG. 8 graphically presents the triglycerides concentration in the bloodstream (mg·dL$^{-1}$) for healthy volunteers that have been subjected to a diet rich in carbohydrates and fats for one week, before and after the intake of sugar water (A) or a drink made from micro filtrated black berry juice (B).

FIG. 8 demonstrates a decrease in some lipid profile markers such as triglyceride levels, which were significantly reduced by 20% in the group that took the blackberry beverage, compared to the control group that took sugar water (p=0.0003).

Similarly, a decrease was identified in enzyme activities that neutralize the toxicity of oxygen reactive species, when an organism is subjected to oxidative stress, such as superoxide dismutase (SOD) and catalase (CAT), whose activities were reduced by 27% and 36%, with p=0.001 and p=0.013, respectively.

This clinical trial demonstrated that the ingestion of a drink made from microfiltered blackberry juice provides a protective effect against oxidative stress induced in healthy volunteers, who ate a diet rich in fat and carbohydrates.

These results show that the consumption of a beverage made from microfiltered blackberry juice is beneficial to human health.

Example 8. The Protective and Restorative Effect of Microfiltered and Ultrafiltered Blackberry Juices on Damage Caused by UVB Radiation We evaluated the potential chemopreventive effect of aqueous preparations of the microfiltered and ultrafiltered blackberry juices on skin cell damage caused by exposure to UV radiation. The purpose of this study was to review the protective effect of the extract obtained by the method of the invention so as to develop new topical products based on said extract for the prevention and/or treatment of skin cancer.

Figure 9:
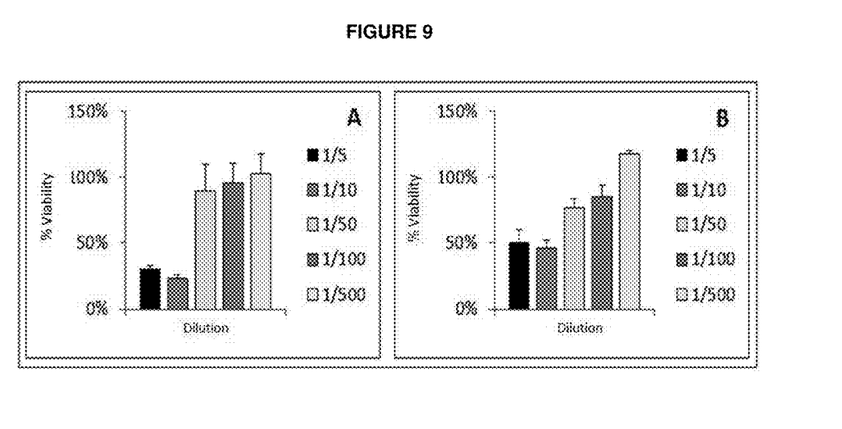
FIG. 9 shows the cytotoxic effect of the microfiltered (A) and ultrafiltered (B) blackberry juices (A) at different dilutions on cultured 3T3 murine fibroblasts. It shows the average of 3 replicates for each treatment. The viability rate was calculated based on the absorbance (570 nm) obtained through MTT staining.

To this effect, the cytotoxic effect of said juice was characterized in vitro on dermis skin cells of an albino mouse (3T3 murine fibroblasts) cultured with DMEM (4.5 g/L glucose) fetal bovine serum at 7%, glutamine (4 mM) at 2%, penicillin-streptomycin (10 000 u/ml penicillin G, 10 000 µg/ml streptomycin sulfate) at 1% and sodium pyruvate (0.11 mg/ml) at 1%. In the same culture medium or PBS, dilutions of 1/5, 1/10, 1/50, 1/100 and 1/500 of the microfiltered and ultrafiltered juices were prepared, of which the 3T3 cells (70-80% confluence) were treated for 24 hours. The cytotoxicity of the juices was determined by its effect on cellular viability determined by MTT staining (Freshney, I. 2005. Culture of animal cells: A manual of basic technique. 5ta Ed. John Wiley & Sons. New Jersey, USA. p. 580) after 24 hours of treatment, where the absorbance of the sample (570 nm) is proportional to the amount of viable cells. The data demonstrated that the 1/50 dilution and the 1/100 dilution of the microfiltered blackberry juice in culture medium reduced cell viability by 10% and 4%, respectively, while the same dilutions of the ultrafiltered juice in culture medium reduced the same parameter by 24% and 14%, respectively (FIG. 9).

Similarly, the 1/50 and 1/100 dilutions of both the microfiltered and the ultrafiltered juice, were used to treat 3T3 cells (70-80% confluence) during and after 30 minutes of exposure to UVB radiation (280-320 nm) at 20 cm from the source (UVML-28 EL, UVP), in order to assess whether there is a possible protective and/or restorative effect, respectively, of damage caused by this type of radiation.

For the protective treatment, the cells were irradiated in the dissolved juices in PBS and immediately placed in the culture medium. For the restorative effect, the cells were irradiated in PBS and immediately placed in the respective dilutions of the juices in the culture medium. Cell viability was determined 24 hours after irradiation through MTT and 3T3 cells irradiated in PBS under the same conditions described above were used as the control.

Figure 10:
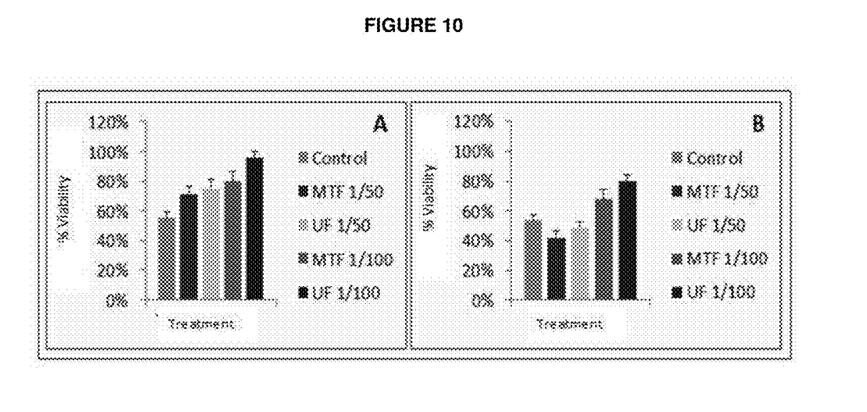
FIG. 10 shows the protective (A) and restorative (B) effects of the microfiltered (MTF) and ultrafiltered (UF) blackberry juices at different dilutions on 3T3 murine fibroblasts treated with UVB (30 min). It shows the average of 3 replicates for each treatment. The viability rate was calculated based on the absorbance (570 nm) obtained through MTT staining. The control refers to 3T3 cells treated with UVB, without blackberry juice.

The results demonstrated that both the ultrafiltered and microfiltered juices provide both protective and restorative effects on damage caused by UVB irradiation (FIG. 10), where the ultrafiltered juice at a 1/100 dilution was most effective in all cases, with a recovery of 32% of cell viability compared to the control in the restorative treatment, and a recovery of 38% of cell viability compared to the control in the protective treatment. Furthermore, the trends seem to show a greater protective effect than a restorative one.

All cells in all assays were inoculated at the same cell concentration and were maintained under the same conditions for the same amount of time (37° C., 5% CO2).

These trials demonstrate that ultrafiltered blackberry juice and microfiltered blackberry juice in the appropriate dilution present low cytotoxicity in skin cells, and that topical application can protect and repair damage caused by the UVB component of sunlight, hence its potential use in cosmetic compositions.

Example 9. Antioxidant Capacity of the Extract Rich in Polyphenols Obtained from Microfiltered Blackberry Juice We confirmed the removal activity of the polyphenol rich extract from microfiltered blackberry juice using different methods (Chart 11), and this activity was compared with the flavonoid remover of quercetin radicals.

CHART 11

Antioxidant capacity of the blackberry extract and quercetin

|  | DPPH $IC_{50}$ (µg/mL) | ORAC µM TE/g | No Removal $IC_{50}$ (µg/mL) |
|---|---|---|---|
| Blackberry Extract | $2.57 \pm 0.11^a$ | $4339 \pm 144^a$ | $24.5 \pm 1.3^a$ |
| Quercetin | $2.17 \pm 0.08^b$ | $2067 \pm 81^b$ | $6.57 \pm 0.8^b$ |

Each value is the mean ± DE of three replicate experiments. The means in columns followed by different letters presented significant differences (p < 0.05).

Example 10. Inhibition of Lipid Peroxidation

Figure 11:
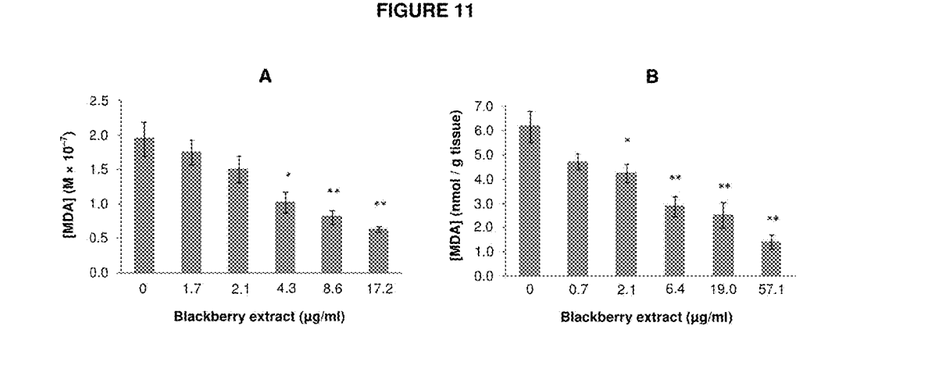
FIG. 11 shows the protective effect of the blackberry extract on oxidative stress induced in liposomes (A) and liver homogenates (B). Each value is the mean±DE (three independent experiments). * $p<0.05$, ** $<0.01$ compared to the controls not treated with the blackberry extract.

To assess the inhibition of lipid peroxidation, lecithin liposomes were incubated with blackberry extract and exposed to oxidative stress induced by AAPH. Compared with the control liposomes, the extract significantly decreased lipid peroxidation based on the 4.3 mg/mL. The IC50 was 7.0±0.5 mg/mL (FIG. 11A). A similar effect of inhibition of lipid peroxidation was assessed in rat liver homogenates where oxidative stress was induced with TBHP. The blackberry extract decreased the levels of lipid peroxidation in a dose dependent manner, with significant differences based on the 2.1 mg/mL concentration (FIG. 11B). The amount of extract required to reduce 50% of the concentration of MDA with respect to the control liver tissue was 26.5±2.5 ug/mL.

Example 11. Inhibition of Superoxide Production

Figure 12:
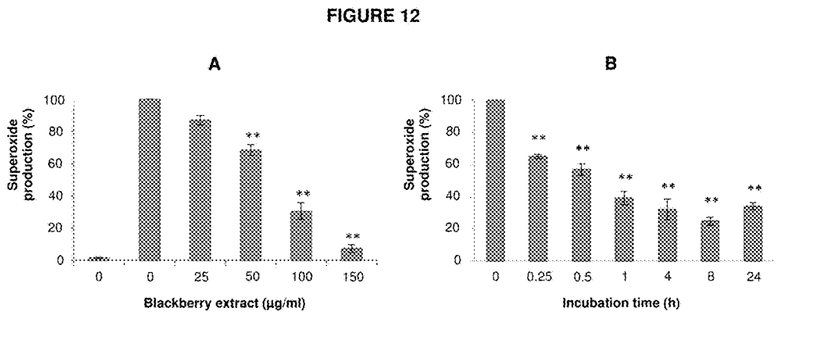
FIG. 12 shows the inhibitory effect of the blackberry extract on induced superoxide production in THP-1 cells: (A) Dose-response assay (B) Kinetic assay. Each value is the mean±DE (four independent experiments).* $p<0.05$, ** $<0.01$ compared to the controls not treated with the blackberry extract.

The Exposure of THP-1 cells to PMA resulted in an increase in the production of superoxide that could be recorded with a luminometer. The pre-incubation of blackberry extract with THP-1 cells suppressed the development of fluorescence in a concentration dependent manner (FIG. 12A). The decrease was significant for the 50 ug/mL concentration. The IC50 value was 80.3±4.1 mg/mL for 24 h of incubation of the extract. The kinetics of the inhibition activity of superoxide of the blackberry extract is carried out with a single concentration of 80 ug/mL (FIG. 12B). Even a short incubation time of 15 min, showed a significant inhibition (p<0.05) of 35% in the production of superoxide. Maximum inhibition (76%) is observed after 8 h of incubation.

Example 12. Inhibition of NO Production

Figure 13:
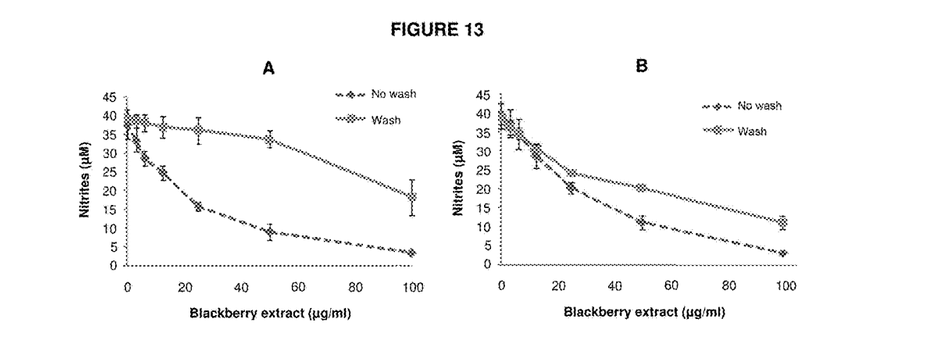
FIG. 13 shows the effect of the blackberry extract on nitrite production induced by LPS+IFNγ: (A) 4 hour pre-treatment with blackberry extract, (B) 24 hour pre-treatment with blackberry extract. The data is expressed as the mean±DE based on three different experiments, performed in triplicate.

In order to assess the ability of the extract to inhibit nitrite production, J774 macrophage cells were treated with the blackberry extract for 4 (FIG. 13A) or 24 hours (FIG. 13B) and then were exposed to LPS+IFNγ. In some experiments the extract was removed before treatment with LPS+IFNγ.

Four hours of pretreatment with the blackberry extract reduced NO production in a dose dependent manner only when the LPS+IFNγ was incubated with the extract (no wash). If the extract is removed before the addition of LPS+IFNγ (with rinsing), inhibition of NO production was seen only in the highest concentration tested. The IC50 value with an incubation time of 4 hours was 24.4±3.2 ug/mL and 99.1±7.3 ug/mL, in non-washed and washed conditions, respectively. This difference suggests that with the 4 hours of incubation, the extract has only one removal activity, as confirmed in the assay of NO removal.

From the above examples it can be concluded that the blackberry extract obtained by the method of the invention shows a potentially beneficial effect on the ability to protect against oxidative stress and inflammatory processes. These activities are in large part due to the fact that the most important molecules of the extract have powerful antioxidant activities, making it very attractive for obtaining pharmaceutical compositions useful in treating conditions involving inflammatory and/or oxidative stress processes are involved.

The invention claimed is:

1. A method for obtaining an ellagitannin extract with a concentration of at least 50% ellagitannins, on a dry weight basis, from fruits containing ellagitannins, wherein the method comprises the steps of:
   (I): pressing fruit or fruit waste thereof, wherein said fruit or fruit waste thereof contains ellagitannins, to obtain a liquid fraction, and treating the liquid fraction with enzymes, wherein the enzymes are added to said liquid fraction to provide an enzyme-treated liquid fraction;
   (II): clarifying the enzyme-treated liquid fraction obtained in step (I) with tangential microfiltration to provide a permeate;
   (III): fractionating the permeate obtained in step (II) by membrane separation, wherein said membrane separation is ultrafiltration or nanofiltration to provide a retentate;
   (IV): purifying the retentate by diafiltration to provide a purified ellagitannin extract; and
   (V): concentrating the purified ellagitannin extract obtained in step (IV) to provide the elagitannin extract.

2. The method according to claim 1, wherein the pressing is carried out continuously or discontinuously, at a pressure between 2,000 and 10,000 kPa, for 5 to 40 minutes, against a mesh having an aperture size between 0.2 and 1 mm.

3. The method according to claim 1, wherein the enzymes are selected from the group consisting of cellulolytic enzymes, pectinolytic enzymes, or mixtures and combinations thereof.

4. The method according to claim 1, wherein step (I) further comprises acidification of the fruit waste to a pH between 3.0 and 5.0 with acidified water.

5. The method according to claim 1, wherein the tangential microfiltration is carried out with a membrane with a pore size between 0.05 and 1.0 μm.

6. The method according to claim 5, wherein the membrane is organic or inorganic.

7. The method according to claim 5, wherein the tangential microfiltration is carried out at a tangential speed between 4 and 7 m·s$^{-1}$, with at a transmembrane pressure between 120 and 350 kPa and a temperature between 25 and 50° C.

8. The method according to claim 1, wherein the ultrafiltration or nanofiltration in step III is carried out using a membrane with a filtration capacity between 0.1 and 50 kDa.

9. The method according to claim 8, wherein the membrane is organic or inorganic, and has a tubular or flat shape.

10. The method according to claim 1, wherein
   ultrafiltration and nanofiltration are carried out at a transmembrane pressure between 250 and 4,000 kPa, a tangential speed between 0.2 and 4 m·s$^{-1}$, and a temperature between 25 and 50° C.

11. The method according to claim 1, wherein ultrafiltration and nanofiltration is carried out until a volume reduction factor (VRF) between 5 and 30 is reached.

12. The method according to claim 1, wherein the purification in step (IV) is carried out through diafiltration.

13. The method according to claim 12, wherein diafiltration is carried out using a membrane with a filtration capacity between 0.1 and 50 kDa.

14. The method according to claim 13, wherein the membrane for diafiltration is organic or inorganic, and has a tubular or flat shape.

15. The method according to claim 12, wherein diafiltration is carried out at a transmembrane pressure between 250 and 4,000 kPa, a tangential speed between 0.2 and 4 m·s$^{-1}$, a temperature between 25 and 50° C. and at a constant volume.

16. The method according to claim 12, wherein diafiltration is carried out until reaching a purity of 90% for ellagitannins.

17. The method according to claim 1, wherein the purified ellagitannin extract is concentrated by reverse osmosis, osmotic evaporation, or a combination thereof.

18. The method according claim 1, wherein the purified ellagitannin extract is concentrated by vacuum evaporation.

19. The method according to claim 2, wherein the fruit is, or the fruit waste is from fruit selected from the group consisting of pomegranates, raspberries, strawberries, grapes, blackberries, and fruits from the *Rubus* genus.

20. The method according to claim 19, wherein the fruit is or fruit waste is from a tropical mountain blackberry *Rubus adenotrichos* Schltdl. or *Rubus glaucus*.

* * * * *

UNITED STATES PATENT AND TRADEMARK OFFICE
CERTIFICATE OF CORRECTION

PATENT NO. : 10,278,949 B2
APPLICATION NO. : 14/117282
DATED : May 7, 2019
INVENTOR(S) : Oscar Gerardo Acosta Montoya et al.

Page 1 of 1

It is certified that error appears in the above-identified patent and that said Letters Patent is hereby corrected as shown below:

In the Claims

Column 18, Line 48, Claim 19:
After "selected from"
Delete "the" and
Insert -- a --.

Signed and Sealed this
Twenty-ninth Day of October, 2019

Andrei Iancu
*Director of the United States Patent and Trademark Office*